United States Patent [19]
Van Der Walt

[11] Patent Number: 5,198,765
[45] Date of Patent: Mar. 30, 1993

[54] METHOD OF AND APPARATUS FOR SIMULTANEOUSLY TESTING A WIRE ROPE FOR MULTIPLE DEFECTS

[76] Inventor: Nicolaas T. Van Der Walt, 21 Denton Place, Kibler Heights, Johannesburg, Transvaal, South Africa

[21] Appl. No.: 788,525

[22] Filed: Nov. 6, 1991

[30] Foreign Application Priority Data

Nov. 7, 1990 [ZA] South Africa .................. 90/8910

[51] Int. Cl.⁵ .................. G01N 27/72; G01N 27/82; G01R 33/12
[52] U.S. Cl. .................. 324/227; 324/242
[58] Field of Search .............. 324/227, 238, 239, 240, 324/241, 242, 243

[56] References Cited

U.S. PATENT DOCUMENTS

| | | | |
|---|---|---|---|
| 3,378,761 | 4/1968 | Morgan | 324/37 |
| 3,881,151 | 4/1975 | Bigelow, Jr. | 324/37 |
| 4,495,465 | 1/1985 | Tomaiuolo et al. | 324/232 |
| 4,929,897 | 5/1990 | Van Der Walt | 324/240 |
| 5,036,277 | 7/1991 | Van Der Walt | 324/235 |

FOREIGN PATENT DOCUMENTS

| | | |
|---|---|---|
| 60696/80 | 2/1981 | Australia . |
| 121084 | 10/1984 | European Pat. Off. . |
| 127443 | 12/1984 | European Pat. Off. . |
| 1032556 | 6/1985 | Fed. Rep. of Germany . |
| 2350600 | 12/1977 | France . |
| 696369 | 11/1979 | U.S.S.R. . |
| 1270748 | 4/1972 | United Kingdom . |
| 1539313 | 1/1979 | United Kingdom . |
| 2012966 | 8/1979 | United Kingdom . |
| 2071331 | 9/1981 | United Kingdom . |
| 2100440 | 12/1982 | United Kingdom . |
| 2115558 | 9/1983 | United Kingdom . |

*Primary Examiner*—Walter E. Snow
*Attorney, Agent, or Firm*—Barnes & Thornburg

[57] ABSTRACT

A wire rope is tested simultaneously for multiple types of defects by magnetically saturating the rope at two locations in one sense and at an intermediate location in an opposite sense. A sensing coil at any of these locations detects cross sectional area variations in the rope. Two sensing coils positioned respectively between each pair of adjacent locations defect contact pattern variations in the rope. Broken wires are detected by two coils located respectively on opposing sides of the intermediate location and spaced apart by a distance which equals the radius of the coils.

8 Claims, 10 Drawing Sheets

METHOD OF AND APPARATUS FOR SIMULTANEOUSLY TESTING A WIRE ROPE FOR MULTIPLE DEFECTS

BACKGROUND OF THE INVENTION

This invention relates to the electro-magnetic testing of a wire rope.

The applicant's European patent No. 87810158.3 describes a procedure for simultaneously testing a wire rope to determine variations in three characteristics, namely the cross sectional area of the rope, the wire contact pattern within the rope, and the existence of broken wires. Use is made of a magnetic test head which establishes two magnetic fields which magnetize adjacent sections of the rope in opposing directions. The rope is caused to move along a path through the head and the existence of the three characteristics referred to is detected by means of suitable sensors located at positions defined relatively to the head.

When the aforementioned head is operated the various sensors are positioned close to the rope at optimum locations. The rope moves relatively slowly to the test head under controlled conditions during the testing process.

If the test head is left in situ and the wire rope is used for normal operation, and travels at normal operating speeds, then the test head, or the rope, may be damaged by the lateral movement of the wire rope which takes place when the rope speed is increased. If use is made of guides such as rollers or the like to stabilize the rope when it passes through the test head, unnecessary wear may be caused to the rope.

SUMMARY OF THE INVENTION

The present invention is concerned with apparatus for testing a wire rope for one or more of the aforementioned characteristics, which is relatively compact and which can, if desired, be left in situ as a permanent tester. The scope of the invention is not, however, restricted in this way and the apparatus of the invention can be used with equal effectiveness as a portable rope testing device.

The invention provides apparatus for testing a wire rope for cross sectional area variations which includes a magnetizing head for establishing a magnetic field, means for forming a pathway for the rope which permits the rope to travel in an axial direction through the magnetic field whereby the rope is magnetically saturated in a first sense at a first location, and in a second sense which is opposite to the first sense at a second location and at a third location, the second and third locations being respectively positioned on opposing sides of the first location, and at least a first sensing means positioned at a respective one of the first, second and third locations for detecting a magnetic flux variation in the rope.

A magnetic flux variation detected by the first sensing means, positioned as indicated, is attributable to a cross sectional area variation in the rope.

The apparatus may be used for simultaneously testing the wire rope for contact pattern variations and, for this purpose, may include at least second and third sensing means which are positioned between the first and second locations, and the first and third locations, respectively, each of the second and third sensing means being at a respective region where the flux density in the rope is approximately zero and being used for measuring the rate of change of flux density, as a function of rope length.

The second and third sensing means, used in the manner indicated, detect variations in the rate of change of flux density which are attributable to contact pattern variations in the rope.

Each of the first, second and third sensing means may comprise any suitable device. These sensing means may for example be coils and may be positioned so that they extend circumferentially around the wire rope.

The apparatus may include fourth sensing means and the first and fourth sensing means may be positioned respectively at any two of the first, second and third locations. The fourth sensing means acts in the same way as the first sensing means in that it is responsive to magnetic flux variations in the rope which are attributable to cross sectional area variations in the rope. Signals produced by the first sensing means and the fourth sensing means may be added for example by connecting the first sensing means and the fourth means in series.

The apparatus of the invention may also be used for simultaneously testing the wire rope for broken wires and for this purpose may include two coils, each of a first radius, which are spaced apart by a distance which is approximately equal to the first radius and which are respectively positioned on opposing sides of the first location, the two coils being used to detect magnetic flux variations.

Magnetic flux variations which are detected by the said two coils are attributable to the effect of broken wires in the wire rope.

Signals produced by the two coils may be integrated with respect to time, and may be further processed in any appropriate manner, to enhance the possibility of detecting signals of relatively low levels in background noise which is generated during the passage of the rope along the pathway.

The invention further extends to a method for testing a wire rope for cross sectional area variations which includes the steps of establishing a magnetic field, causing the wire rope to move in an axial direction along a pathway through the magnetic field whereby the rope is magnetically saturated in a first sense at a first location, and in a second sense which is opposite to the first sense at a second location and at a third location, the second and third locations being respectively positioned on opposing sides of the first location, and detecting magnetic flux variations in the rope at least at one of the first, second and third locations.

Magnetic flux variations which are detected at any of the first, second and third locations are attributable to cross sectional area variations in the rope.

Magnetic flux variations may be detected at least at two or if desired at all three, of the said locations and the signals which are produced, upon detecting magnetic flux variations, may be added.

The method of the invention may be used for simultaneously testing the wire rope for contact pattern variations by detecting the rate of change of flux density, as a function of rope length, at each of two regions, where the flux density in the rope is approximately zero, the two regions being positioned respectively between the first and second locations, and the first and third locations.

Variations in the rate of change of flux density, as a function of rope length, are attributable to contact pattern variations in the rope.

The method may also be used for simultaneously testing the wire rope for broken wires by using at least two coils which are positioned on opposing sides of the first location respectively, the coils being spaced apart by a distance which is approximately equal to the radius of the coils, and with the coils being responsive to flux density variations.

Coils of the kind described, used in the way indicated, detect broken wires in the rope.

BRIEF DESCRIPTION OF THE DRAWINGS

The invention is further described by way of example with reference to the accompanying drawings in which.

DESCRIPTION OF PREFERRED EMBODIMENT

Figure 1:
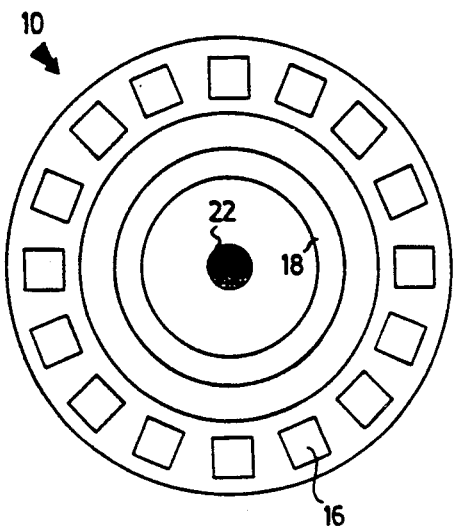
FIG. 1 is an end view of a magnetizing head used in the apparatus of the invention.
Figure 2:
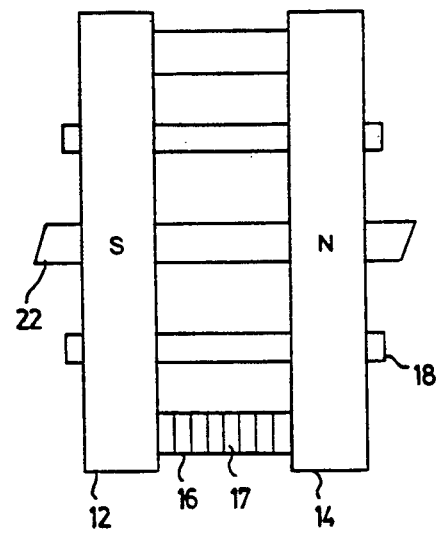
FIG. 2 is a side view of the magnetizing head of FIG. 1, FIGS. 3 and 4 respectively show a pole piece and a magnet which are suitable for use in the magnetizing head of FIGS. 1 and 2.

FIGS. 1 and 2 illustrate a magnetizing head 10 from the end and from the side respectively.

The head 10 includes pole pieces 12 and 14 respectively, which are of annular shape, and which have, in this example, sixteen magnet stacks 16 between them.

Each magnet stack 16 includes eight magnets 17 of rectangular outline mounted adjacent one another in a magnetic series configuration. The pole piece 14 is a north pole while the pole piece 12 is a south pole.

A coil insert 18 is positioned inside the assembly of magnet stacks 16. The insert accommodates measuring coils for measurements which are described hereinafter.

The test head defines a circular pathway 20 through which a wire rope 22, which is to be tested, passes. It can be seen that there is a considerable amount of clearance between the rope and the coil insert 18 and this factor makes the test head suitable for permanent installation under conditions where the rope 22 may move by a substantial extent laterally during use. On the other hand the relatively large diameter coils which are used do lead to reduced signal to noise ratios and signal processing techniques may be resorted to in order to identify those contributions to the signals which originate from defects in the rope 22.

Figure 3:
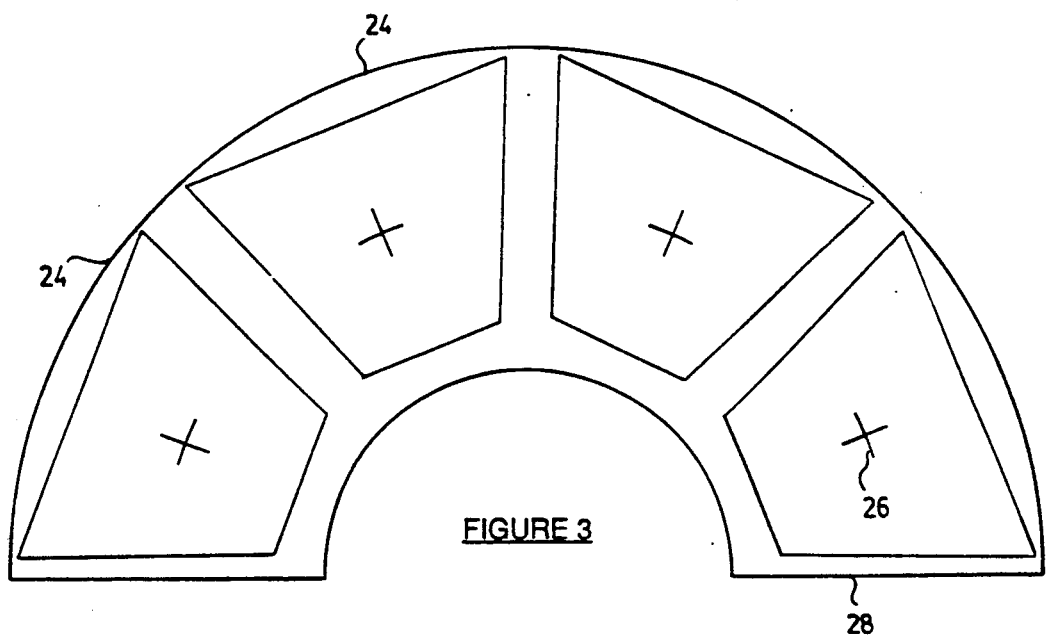
Figure 4:
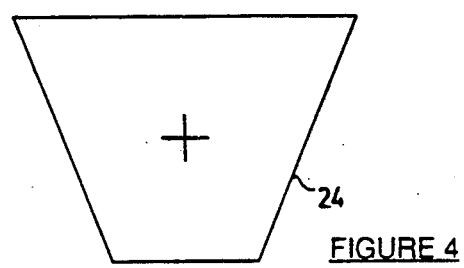
Figure 5:
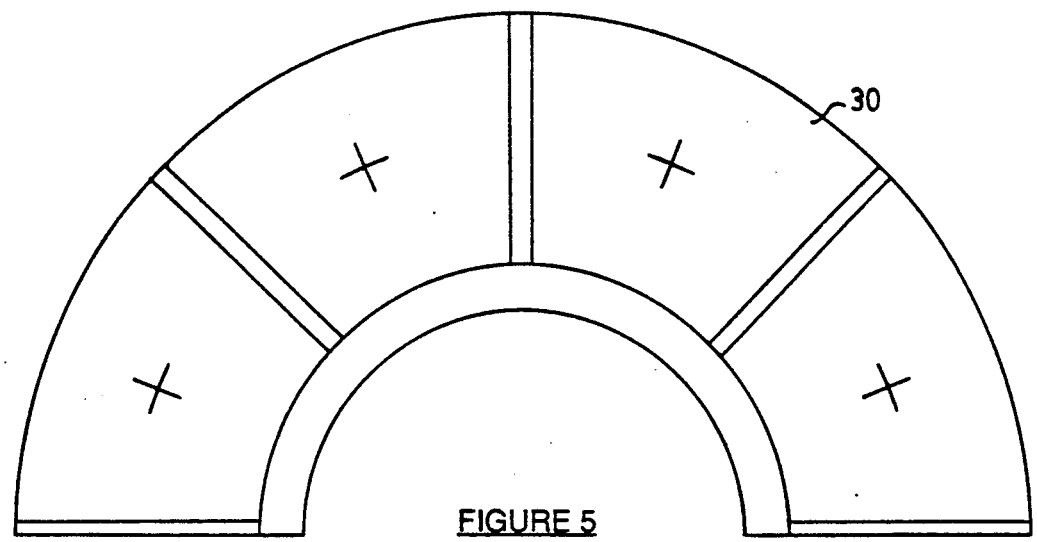
FIG. 5 shows a pole piece with magnets of an alternative shape to that shown in FIG. 4.

As an alternative to the rectangular magnet configuration referred to use may be made of trapezoidal magnets 24, of the kind shown in FIG. 4, which are axially aligned and assembled at locations 26 indicated on a pole piece 28 in FIG. 3. The trapezoidal configuration utilises space more efficiently than rectangular magnets, for a desired magnetic field intensity in the head 10. A more compact arrangement of magnets can in fact be achieved by utilising magnets 30 which are segments of an annulus as shown in FIG. 5.

Figure 6:
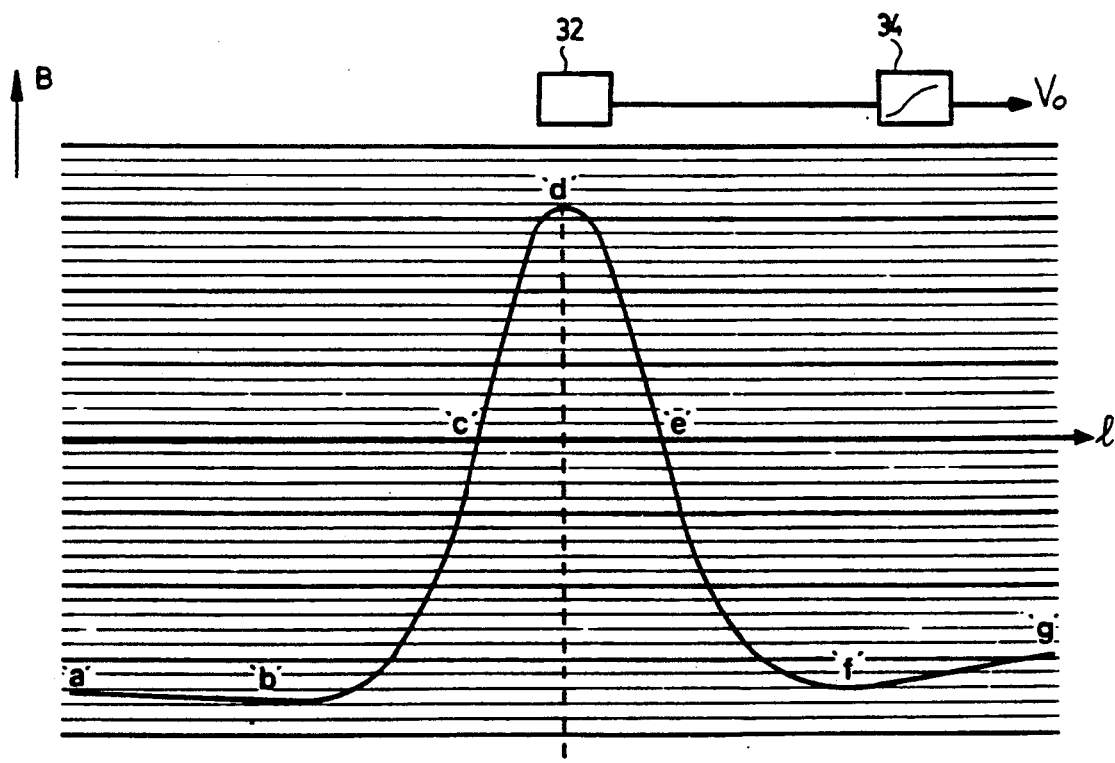
FIG. 6 is a curve of flux density B as a function of rope length, obtained with the magnetizing head of FIGS. 1 and 2.

FIG. 6 is a curve B(l) of flux density B which is produced in the rope 22 by the head 10, as a function of rope length l, relatively to a reference co-ordinate marked O, which is more or less at a central position in the head, at which the flux density in the rope 22 reaches a maximum positive value.

At the location marked d on the curve of FIG. 6, which coincides with the aforementioned reference co-ordinate, the rope is magnetically saturated in a positive sense while at locations marked b and f the rope is magnetically saturated in a negative sense.

At locations c and e the flux density is zero.

The locations b and f are approximately at the axial extremities of the head 10. Away from these extreme points at variable locations a and g within the rope the magnetic flux density is, for practical considerations, substantially saturated, in the negative sense, although at a level which is slightly less than the peak saturation levels at the points b and f.

FIG. 6 schematically shows a measuring coil 32, which is mounted to the coil insert 18, and which extends circumferentially around the rope lying on an axis which passes through the point d. If the rope has a nominal cross sectional area A then the variation in flux, $\Delta\phi$, due to a step function variation in the area $\Delta A$ is given by the following equation:

$$\Delta\phi = \frac{1}{2} B(l) \Delta A \left( \frac{1}{(l^2 + R^2)^{0.5}} + 1 \right)$$

where l is a measurement of the rope length as shown in FIG. 6,

R is the radius of the coil 32, and

B(l) is the flux density in the rope as a function of l.

If the coil 32 has N turns and its output is applied to the input of an integrator 34, shown schematically in FIG. 6, with a time constant T then the integrator output voltage $V_0$ is given by the following equation:

$$V_o = \frac{N}{T} \Delta\phi$$

$$= \frac{N}{2T} B(l)\Delta A \left( \frac{1}{(l^2 + R^2)^{0.5}} + 1 \right)$$

At the location d the rate of change of flux density with respect to rope length, $$\frac{dB}{dl},$$

is zero. Consequently there are no induced eddy currents to disturb the even distribution of flux density in the cross section of the rope. The location d is thus suitable for detecting flux variations which are attributable to cross sectional area variations in the rope.

Figure 7:
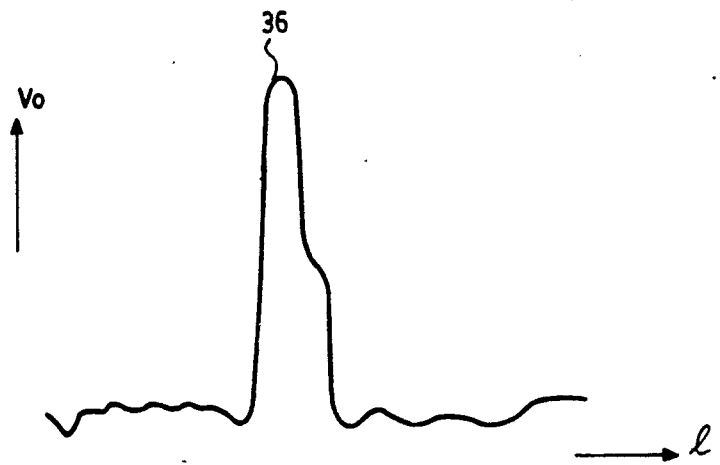
FIG. 7 is a signal produced by an integrator, used with the head of FIGS. 1 and 2, to test a rope which has a cross sectional area variation, FIGS. 8, 9 and 10 respectively show the integrated response of a measuring coil, positioned at different locations in the magnetizing head, to a step function variation in the cross sectional area of the rope under test.

The rope 22 was modified, for test purposes, by tying a number of axially extending wires to an outer surface of a normal section of the rope. The rope was moved axially through the head 10 and the resulting signal produced at the output of the integrator 34 is shown in FIG. 7. The peak in the curve, designated 36, corresponds to the position of the additional wires.

Figure 8:
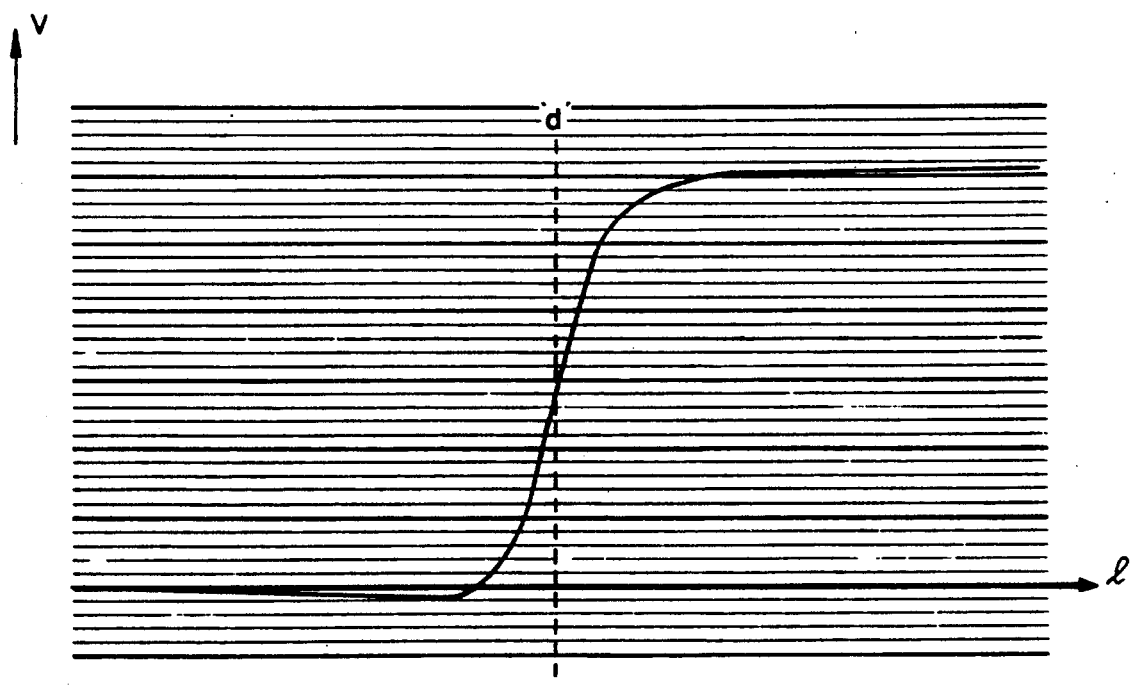

FIG. 8 illustrates the integrated response which is produced by the coil 32, positioned at the location d, when an infinitely long step function variation in the area of the rope occurs as the rope is moved from left to right through the centre of the coil. Once the discontinuity has passed through the plane of the coil the integrator output remains constant.

Figure 9:
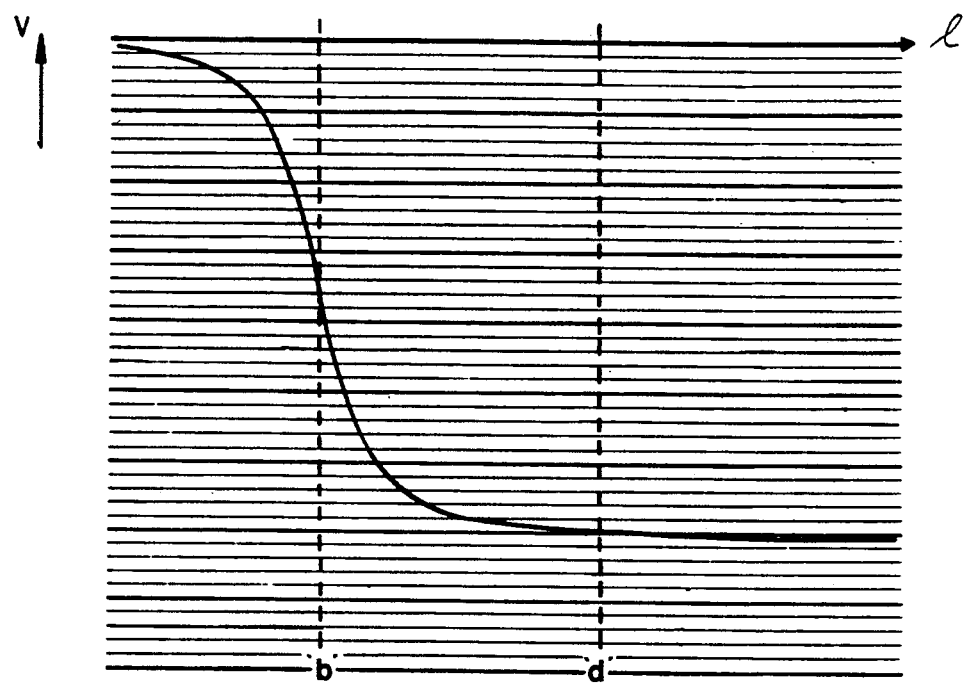

It is apparent that the coil 32 can be positioned at other locations at which the flux density is at a maximum i.e. either of the locations b and f. FIG. 9 shows the integrator output when the measuring coil 32 is at the location b and FIG. 10 shows a similar curve produced by the integrator when the measuring coil is at the location f.

Figure 10:
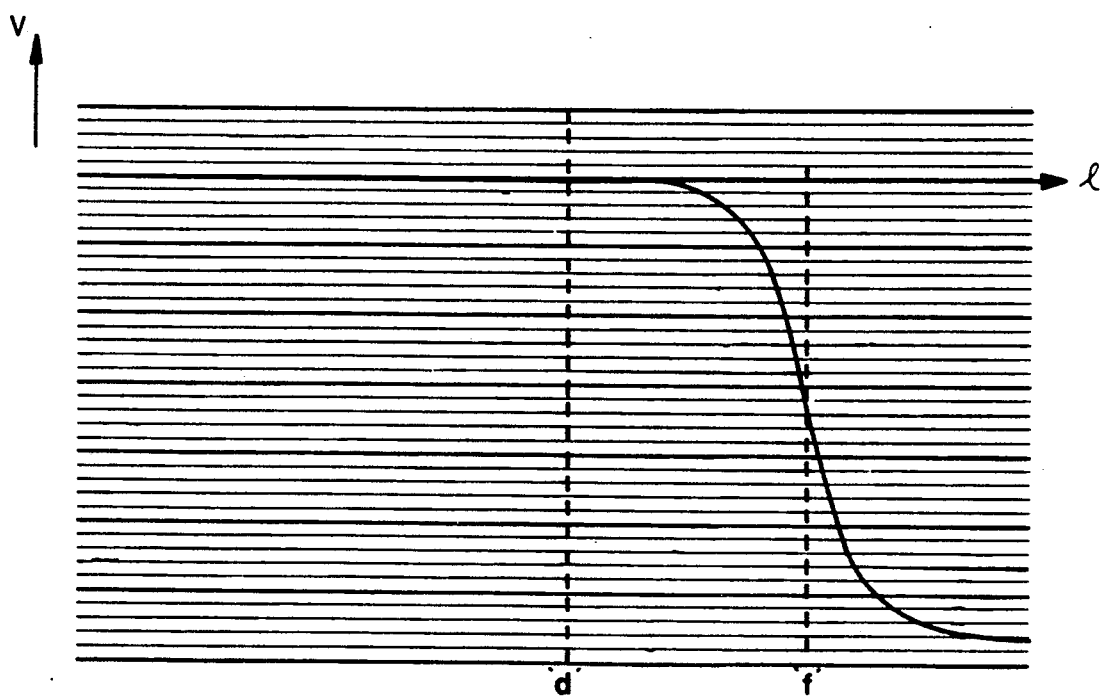
Figure 11:
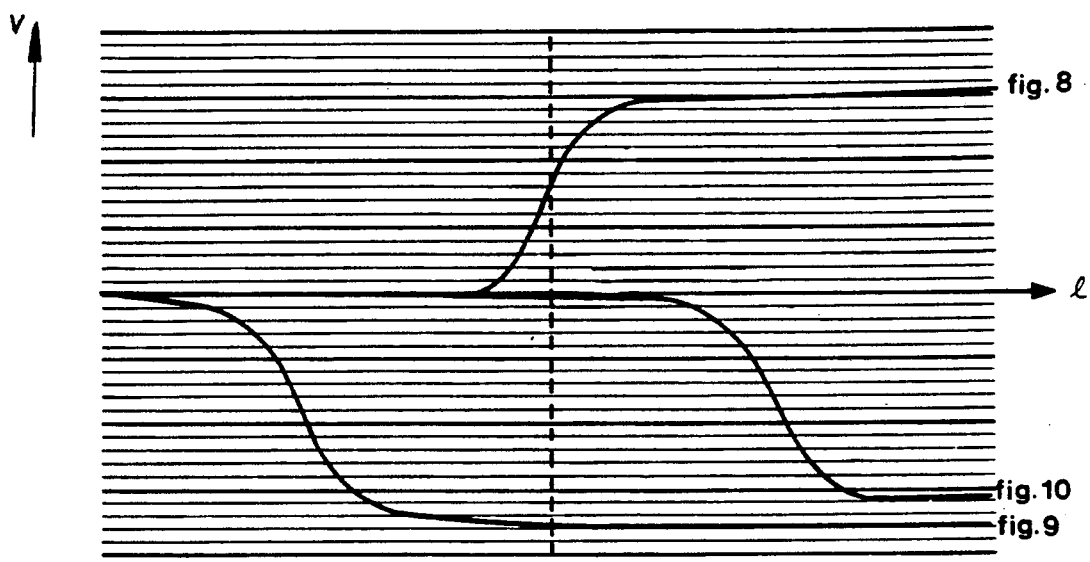
FIG. 11 shows the curves of FIGS. 8, 9 and 10 on common axes.

In each case referred to in connection with FIGS. 8, 9 and 10 the integrator output is proportional to the flux density in the rope. The curves are similar but as is shown in FIG. 11 are axially displaced by an amount which corresponds to the coil position. The measuring coil 32 can be used at any one of the three locations to detect area variations. In each case the discrimination length, which is the accuracy with which the position is detected at which the step function change in the area occurs, is substantially the same and is approximately 400 mm for the given test conditions.

Figure 12:
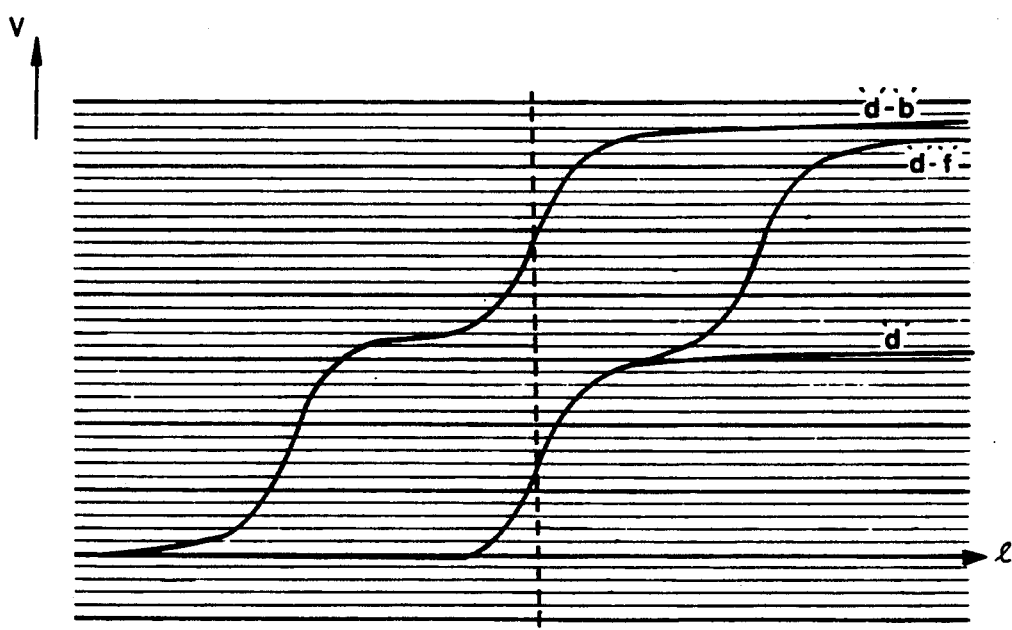
FIGS. 12 and 13 show different curves which result when the signals, which gave rise to the curves of FIGS. 8, 9 and 10, are subtracted from one another.

Use may in fact be made of two or three coils located at the respective locations d, b and f. FIG. 12 shows the effects of the coil at d connected in series opposition with similar coils at b and f respectively, together with the signal which is produced by the coil d.

Figure 13:
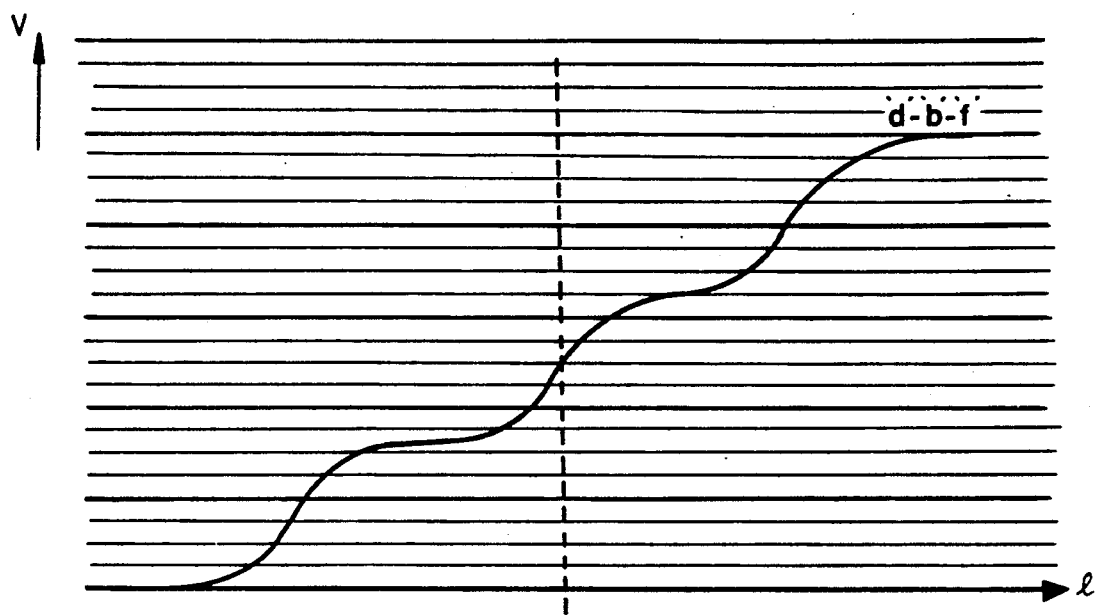

FIG. 13 shows the integrator output when coils at b and f are connected in series opposition to the coil at d.

It is evident from FIGS. 12 and 13 that the measuring sensitivity may be doubled or tripled by using two coil or three coil combinations, but at the expense of the discrimination length. The discrimination length for a two coil system is approximately 1000 mm and that of the three coil system is approximately 1600 mm.

The two coil systems referred to in connection with FIG. 12 are equivalent to saddle coil systems where the half coils are positioned at the locations d and b on the one hand and at the locations d and f on the other hand. It follows therefore that instead of circumferential coils surrounding the rope, of the type designated 32 and described hereinbefore, saddle coils may be used at the locations d and b, or at the locations d and f, to measure area variations.

It can be shown that contact pattern variations can be detected by appropriate measurements taken at a location where the product $$\left( V\mu \frac{dB}{dl} \right)$$

is at a maximum value, and simultaneously B=O, where V is the rope velocity and $\mu$ is the magnetic permeability of the wire rope.

Figure 14:
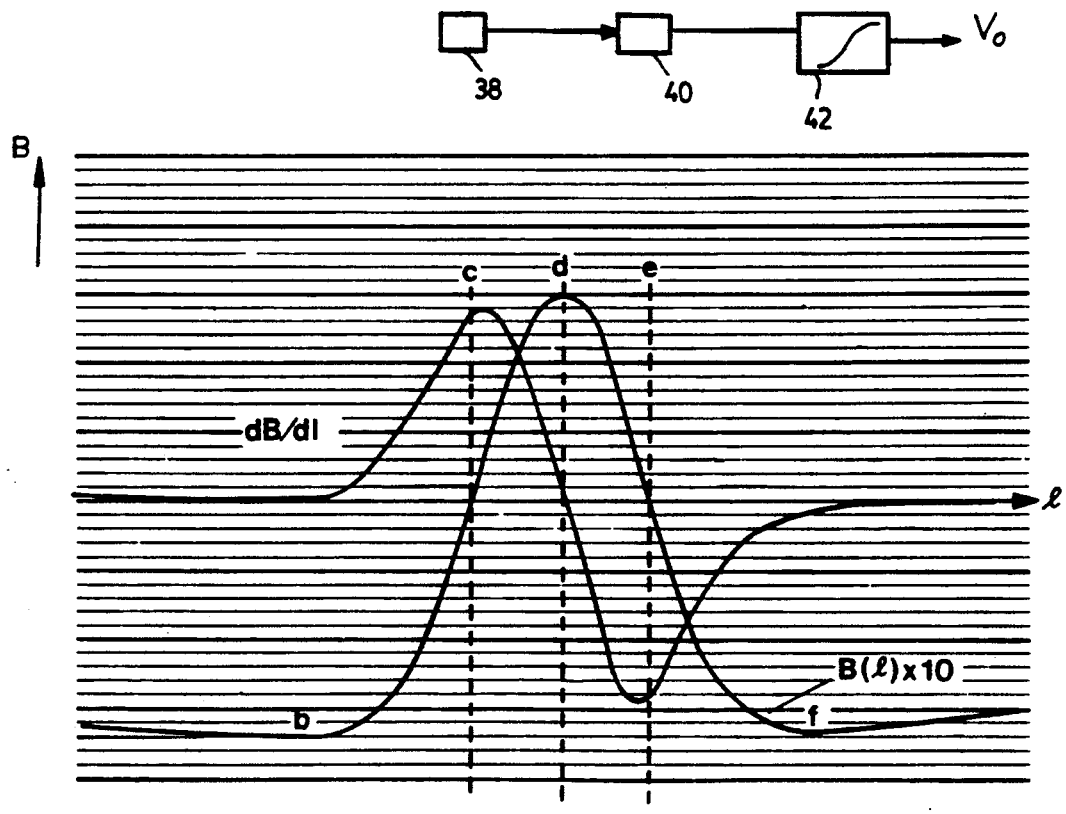
FIG. 14 shows the curve of FIG. 6, which is flux density as a function of rope length relatively to the magnetizing head, multiplied by a factor of 10, together with a curve of the rate of change of flux density as a function of rope length.

FIG. 14 illustrates a curve $$\frac{dB}{dl},$$

together with a curve of flux density B(l) for the test head 10. The curve B(l) is identical to the curve shown in FIG. 6 and is repeated here for ease of reference.

It is to be noted that the locations c and e, at which B=O, do not quite coincide with the peak values of the $$\frac{dB}{dl}$$

curve.

FIG. 14 schematically shows coils 38 and 40 which are positioned more or less at the locations c and e. The optimum positions of these coils are preferably found by experimentation and generally speaking are between the locations at which $$\frac{dB}{dl}$$

is a maximum and the locations c and e respectively.

Figure 15:
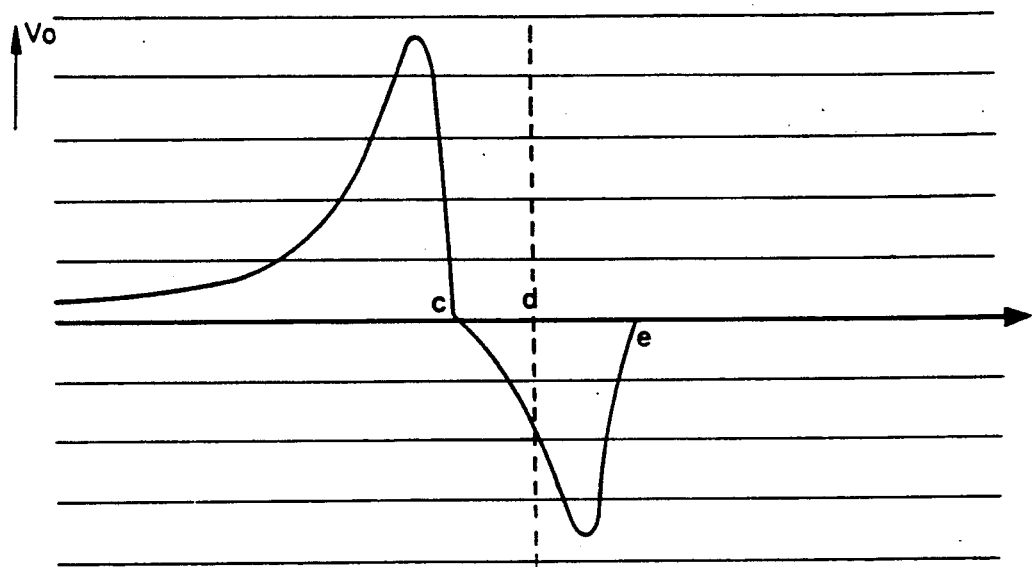
FIG. 15 is an output signal of an integrator connected to two coils, used for detecting contact variations in the wire rope, the output signal being produced in response to an infinitely long area step function in the wire rope.

FIG. 15 shows a curve $V_o$ produced by an integrator 42 connected to the coils 38 and 40, as a function of rope length, when an infinitely long step function variation in area passes through the coils. If the flux densities at the locations c and e are equal, and preferably equal to zero, there is no net integrator output due to the infinitely long area step function but there is a small residual transient pulse.

Figure 16:
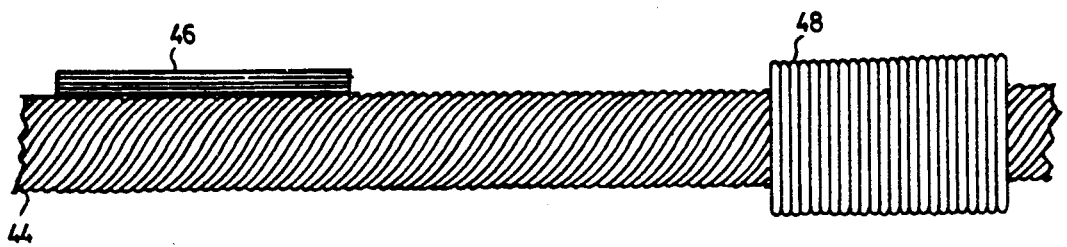
FIG. 16 illustrates modifications which are made to a wire rope for test purposes.

To test the preceding theory and the ability of the system to discriminate between area variations and contact pattern variations a rope 44 was modified in the manner shown in FIG. 16. Four wires 46 of 3.18 mm diameter and approximately 600 mm long and extending in an axial direction were fixed to an external surface of the rope. Approximately one meter away from the wires 46 ten layers of 0.25 mm thick aluminium foil 48, 450 mm long in the axial direction, were wound tightly around the rope.

Eddy currents which are induced in the aluminium foil, when relative movement takes place between the rope 44 and the head 10, simulate a step function increase in contact pattern.

Figure 17:
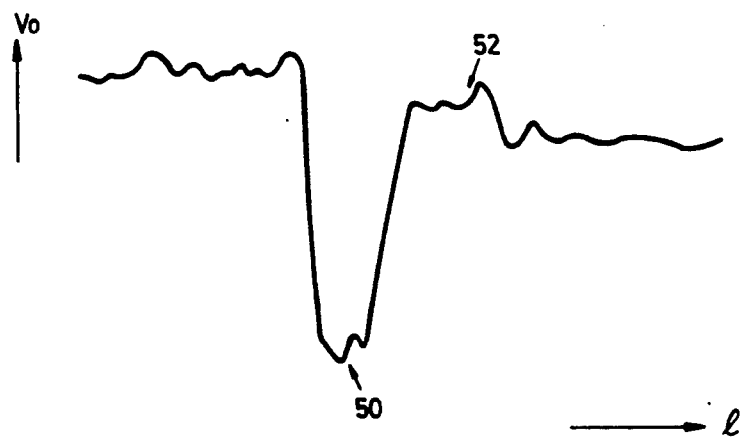
FIG. 17 shows a signal which is produced when the rope of FIG. 16 is passed through the magnetizing head.

FIG. 17 illustrates the output of the integrator 42 for a rope speed of 2 m/sec. The contribution to the signal due to the aluminium foil is a peak designated 50 while the wires 46 produce a peak 52 in the opposite sense.

It can be seen that the contact pattern variation simulated by the aluminium foil is detectable and is distinguishable from the cross sectional area variation which is simulated by the wires 46. The peak 52 is not readily apparent in the background noise and, as has been indicated, it may be necessary to resort to signal processing techniques to enhance the possibility of detecting the peak 52.

Figure 18:
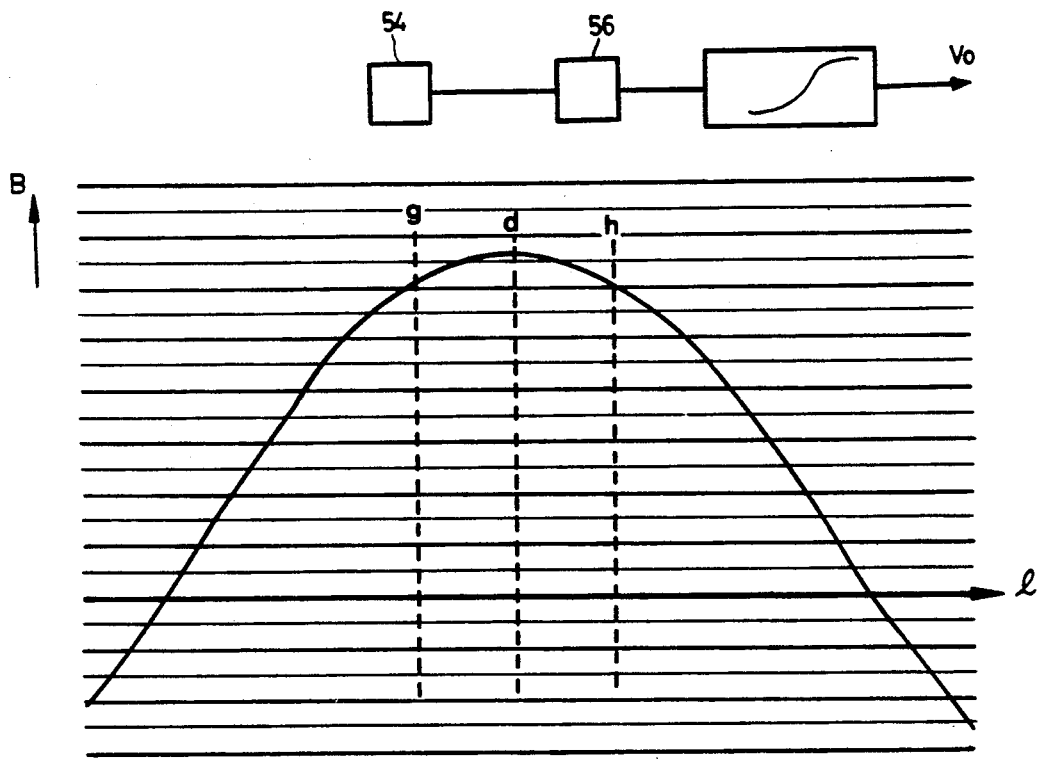
FIG. 18 is an enlarged portion of the curve of FIG. 6 illustrating the position of coils, relatively to the magnetizing head, used for detecting the presence of broken wires in the rope.
Figure 19:
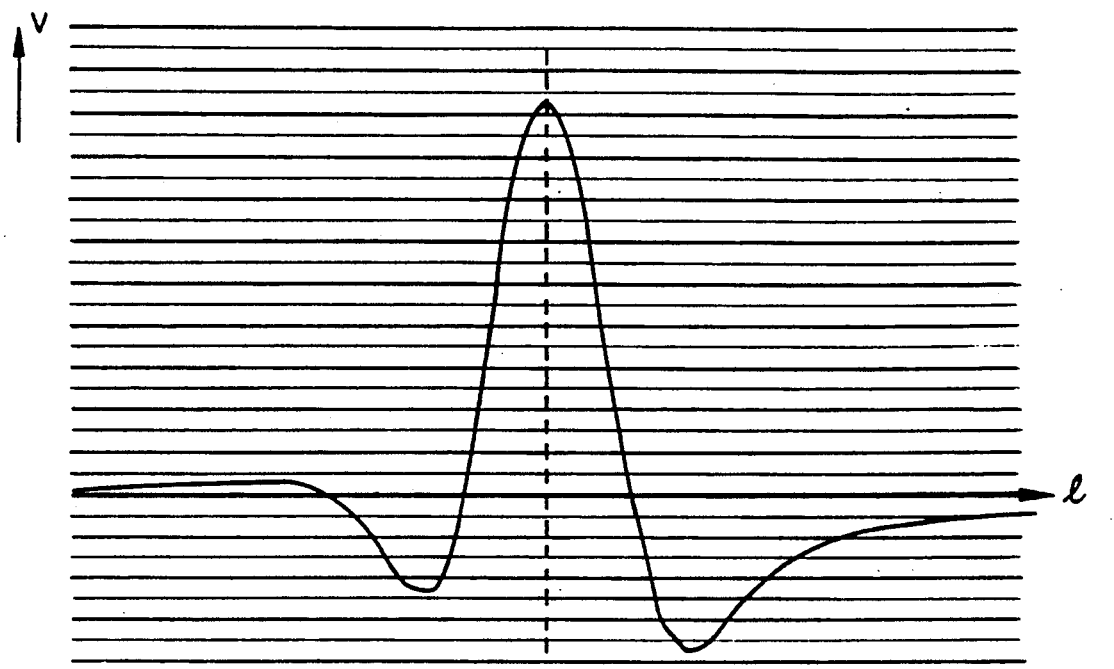
FIG. 19 shows a pulse which is generated by a broken wire in the rope.

FIG. 18 illustrates a portion of the curve of FIG. 6, on an enlarged scale. It can be shown that broken wires in the wire rope under test are detectable by means of two coils 54 and 56 respectively which are positioned at locations g and h, on opposing sides of the location d, with the axial separation between the coils being approximately equal to the radius of the coils which, in this case, is 110 mm. The coils 54 and 56 produce a pulse of the kind shown in FIG. 19, when a broken wire is detected, with the peak value of the pulse being proportional to the number of turns in the coils, the volume of the wire break, and the speed of the rope at the time of testing. The pulse shape does not depend on the number of turns nor on the volume of the wire break.

Figure 20:
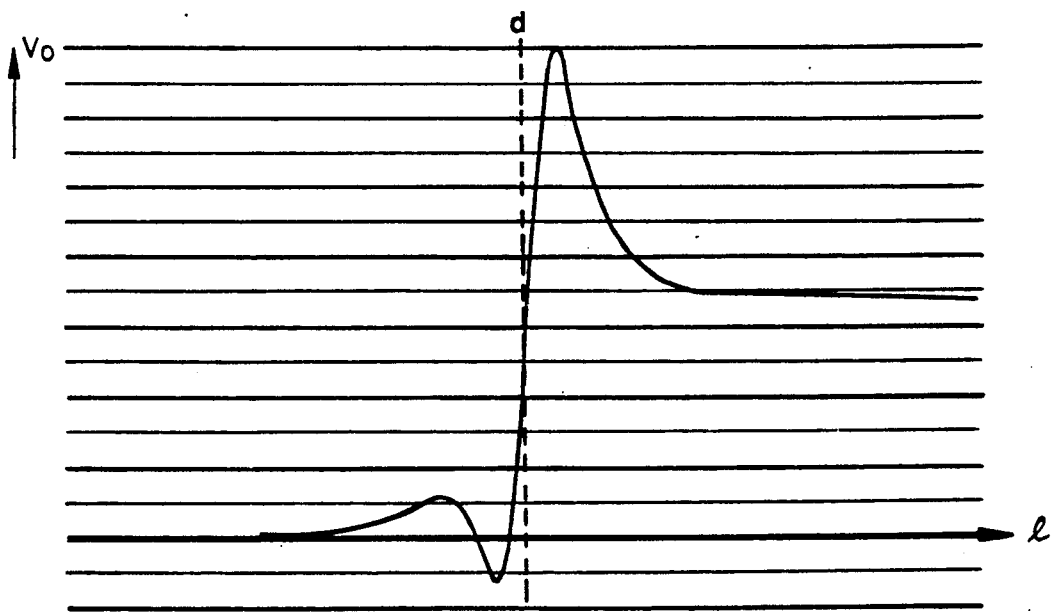
FIG. 20 is the output signal of an integrator to which the pulse of FIG. 18 is applied.

As has been noted the coils which are located in the coil insert 18 have relatively large diameters and consequently the signal to noise ratio for the coils is low. The ability to detect the signal is improved by integrating the broken wires pulses and FIG. 20 shows the output $V_o$ of an integrator connected to the coils 54 and 56. Integration takes place with respect to time and the signal $V_o$ is therefore independent of rope speed.

Figure 21:
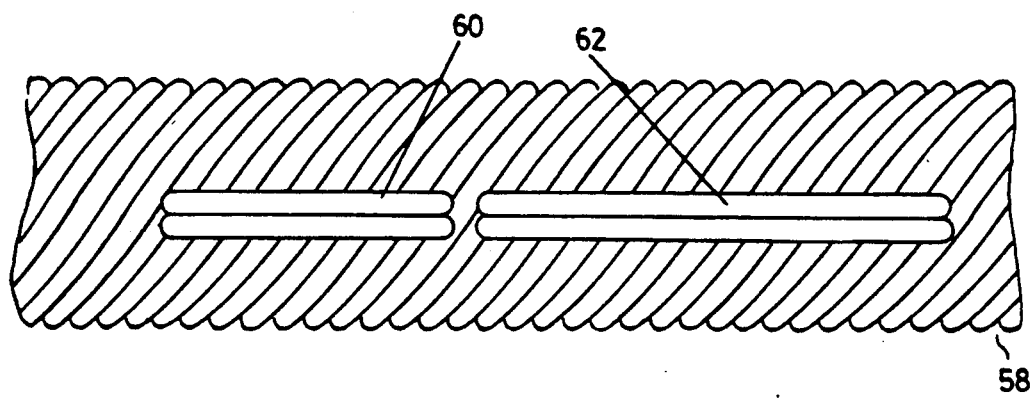
FIG. 21 shows a portion of a rope which is modified to simulate the presence of broken wires.

A large artificial wire break was simulated in a rope 58, as shown in FIG. 21, by tying two sets of wires 60 and 62 to an external surface of the rope, spaced from each other by approximately 10 mm. The arrangement shown in FIG. 21 simulates a wire break volume of approximately 160 mm$^3$.

Figure 22:
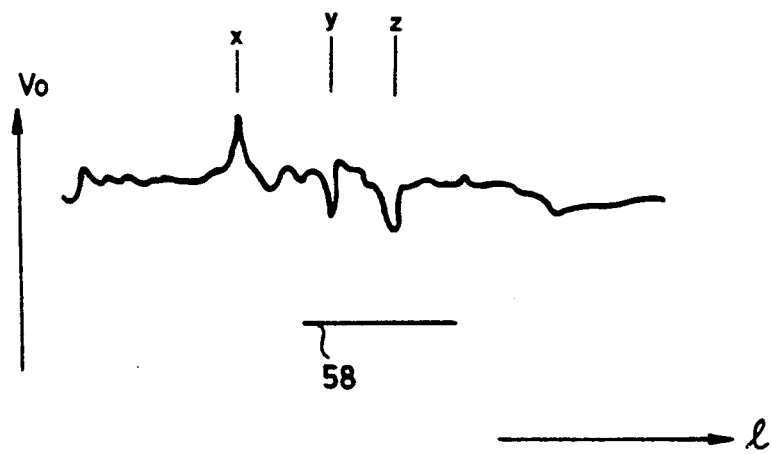
FIG. 22 shows a signal which is produced when the rope of FIG. 20 is passed through the magnetizing head.

The curve shown in FIG. 22 is the output signal of an integrator connected to the coils 54 and 56 and produced when the rope 58 passes through the head 10. The rope 58 is superimposed on the curve. Locations x and z correspond to outer extremities of the wires 60 and 62, and the location y denotes the gap between the two wires.

The effect of the broken wires is discernible although not readily identifiable against the background noise level. The use of cross correlation and pulse shape recognition techniques may be resorted to, together with other methods of signal processing, to enhance and identify the signals produced by the broken wires.

From the preceding description and the accompanying drawings it emerges that the test head 10, together with appropriate and correctly positioned measuring devices, can be used for the simultaneous measurement of area and contact pattern variations, and for the detection of broken wires. The head 10 can be used for a permanent installation or can be embodied in a portable testing device. In the latter case as rope test speeds are generally controlled and are much lower than actual operating speeds, the measuring coils which are used can have smaller diameters than what has been indicated hereinbefore and shown in FIGS. 1 and 2 and consequently larger signal to noise ratios result. Generally speaking therefore as coil diameters increase, relatively to the size of the rope under test, increasing reliance will be placed on signal processing techniques to detect the presence or absence of broken wires, area variations and contact pattern variations.

I claim:

1. Apparatus for simultaneously testing a wire rope for cross sectional area variations and for contact pattern variations which includes a magnetizing head for establishing a magnetic field, means for forming a pathway for the rope which permits the rope to travel in an axial direction through the magnetic field whereby the rope is magnetically saturated in a first sense at a first location, and in a second sense which is opposite to the first sense at a second location and at a third location, the second and third locations being respectively positioned on opposing sides of the first location, a first sensing means positioned at a respective one of the first, second and third locations for detecting a magnetic flux variation in the rope, and second and third sensing means which are positioned between the first and second locations, and the first and third locations, respectively, each of the second and third sensing means being at a respective region where the flux density in the rope is approximately zero and being used for measuring the rate of change of flux density, as a function of rope length.

2. Apparatus according to claim 1 which includes fourth sensing means and wherein the first and the fourth sensing means are positioned respectively at any two of the first, second and third locations.

3. Apparatus according to claim 2 wherein signals produced by the first sensing means and the fourth sensing means are added.

4. Apparatus according to claim 1 which is used for simultaneously testing the wire rope for broken wires and which includes two coils, each of a first radius, which are spaced apart by a distance which is approximately equal to the first radius and which are respectively positioned on opposing sides of the first location, the two coils being used to detect magnetic flux variations.

5. Apparatus according to claim 4 which includes integrator means for integrating signals, with respect to time, which are produced by the two coils.

6. A method for simultaneously testing a wire rope for cross sectional area variations and for contact pattern variations which includes the steps of establishing a magnetic field, causing the wire rope to move in an axial direction along a pathway through the magnetic field whereby the rope is magnetically saturated in a first sense at a first location, and in a second sense which is opposite to the first sense at a second location and at a third location, the second and third locations being respectively positioned on opposing sides of the first location, detecting magnetic flux variations in the rope at least at one of the first, second and third locations, and detecting the rate of change of flux density, as a function of rope length, at each of two regions where the flux density in the rope is approximately zero, the two regions being positioned respectively between the first and second locations, and the first and third locations.

7. A method according to claim 6 wherein the said magnetic flux variations are detected at least at two of the said locations and the signals which are produced, upon detecting magnetic flux variations are added.

8. A method according to claim 6 wherein the wire rope is simultaneously tested for broken wires by using at least two coils which are positioned on opposing sides of the first location respectively, the coils being spaced apart by a distance which is approximately equal to the radius of the coils, and with the coils being responsive to flux density variations.

* * * * *